United States Patent [19]

Debré et al.

[11] Patent Number: 5,236,706
[45] Date of Patent: Aug. 17, 1993

[54] PHARMACEUTICAL PREPARATION FOR THE MATURATION OF PROTHYMOCYTES

[75] Inventors: Patrice Debré, Paris; Mohammad D. Mossalayi, Boussy St. Antoine, both of France

[73] Assignee: Ciba-Geigy Corporation, Ardsley, N.Y.

[21] Appl. No.: 641,971

[22] Filed: Jan. 16, 1991

[30] Foreign Application Priority Data

Jan. 24, 1990 [GB] United Kingdom ............... 9001625

[51] Int. Cl.$^5$ .................. A61K 45/00; C07K 13/00; C07K 15/26
[52] U.S. Cl. ................... 424/85.2; 424/85.1; 514/12; 514/2; 514/8; 514/21; 530/351; 530/350; 435/975; 435/252.33; 935/73
[58] Field of Search ............. 424/85.1; 530/351; 514/8, 12, 21, 2; 435/475

[56] References Cited

U.S. PATENT DOCUMENTS 4,808,611 2/1989 Cosman .......................... 514/12
5,135,851 8/1992 Kojander ......................... 435/34

OTHER PUBLICATIONS

Mossalayi et al. (Mar. 1, 1990) J. Exp. Med. 171(3):959–964.
Mossalayi et al. (May 15, 1990) Blood 75(10):1924–1927.
Mossalayi et al. (1985) J. Immunology 134(4):2400–2404.
Lecron et al. (1989) Exp. Hematol. 17:785–790.
Vercelli et al. (1988) J. Exp. Med. 167:1406–1416.
TeVelde et al. (Apr. 15, 1990), J. Immunology 144:3052–3059.

Primary Examiner—Christopher S. F. Low
Attorney, Agent, or Firm—Irving M. Fishman; Karen G. Kaiser; Barbara J. Ikeler

[57] ABSTRACT

The invention concerns a pharmaceutical preparation comprising the 25K IgE-binding factor (25K IgE-bf) and interleukin-1 (IL-1), and the use of said pharmaceutical preparation for the stimulation of the maturation of prothymocytes, e.g. for the treatment of T cell immunodeficiencies and prothymocyte leukemias.

14 Claims, No Drawings

PHARMACEUTICAL PREPARATION FOR THE MATURATION OF PROTHYMOCYTES

The invention concerns a pharmaceutical preparation comprising the 25K IgE-binding factor (25K IgE-bf) and interleukin-1 (IL-1), and the use of said pharmaceutical preparation for the stimulation of the maturation of prothymocytes, e.g. for the treatment of T cell immunodeficiencies and prothymocyte leukemias.

BACKGROUND OF THE INVENTION

During the development of T-cells, lymphoid stem cells migrate into the thymic rudiment where they proliferate, rearrange their antigen receptor genes, are selected in regard to their MHC-specificity repertoire and differentiate into functionally mature T cells (Refs. 1–6). Prothymocytes having the cell surface marker phenotype $CD7^+CD2^-CD3^-$ represent the earliest identifiable step in T cell lineage (Refs. 7–10). Recent in vitro findings (Refs. 8–11) pointed to the ability of these prothymocytes to acquire mature T cell surface markers following appropriate conditioning. The cellular and factor mediated interactions for this process are poorly understood. A role for cytokines such as IL-1 (Ref. 12) and IL-2 (Ref. 11) was suggested. The ability of IL-1 to function as hemopoietin-1 and to induce development of multipotent hemopoietic cells if it is combined with colony stimulating factors, such as GM-CSF, G-CSF, CSF-1, IL-3, erythropoietin, or erythroid-potentiating activity, is disclosed in the PCT application WO88/00969.

B cells are implied to produce various lymphokines which can intervene in T cell differentiation (Refs. 15, 16). The ability of supernatants derived from PHA induced "B+null" cells (peripheral blood lymphocytes depleted from adherent and mature T cells) to promote in vitro the generation of mature T cell clones from prothymocytes regardless of their anatomical origins was reported (Refs. 8, 13, 14). This prothymocyte differentiating activity (PTDA) was B cell derived (Ref. 14). IL-1 alone had no effect in this respect. However, "B+null" cell-derived supernatants with PTDA always contained low IL-1 levels, whereas neither IL-2, IL-3, IL-4, IL-5, IL-6, GM-CSF, TNF nor IFN-γ were detected in these supernatants (Refs. 8, 14). Biological activities of "B+null" cell-derived supernatants are e.g. the ability to promote the formation of cells able to generate T colony from mature T cell depleted bone marrow, thymus and PBL, the capacity to enhance $CD4^+$ cell derived responses, the ability to increase CFU-GM, CFU-GEMM, and BFU-E numbers in Dexter cultures, the ability to increase the formation of myeloid colonies in cultures of bone marrow cells from patients with refractory anemia, and the ability to induce mature T cell markers on cells derived from some acute lymphoblastic leukemias with prothymocyte features. An example of such an acute lymphoblastic leukemia with prothymocyte features in which the tumor cells have a $CD7^+CD4^-CD8^-$ phenotype was described by Kurtzberg et al. (Ref. 10).

Compounds with PTDA may be useful in the treatment of such leukemias, because the mature T cells derived from the leukemia cells with prothymocyte features may have lost tumorigenicty.

T cell immunodeficiencies can be caused by the incapability of the organism to produce mature T cells or by the loss of mature T cells. T cell immunodeficiences occur e.g. in patients with thymic dysfunctions, after immunosuppressive therapy, in elderly and AIDS patients.

Compounds with PTDA may be useful in the treatment of such T cell immunodeficiencies.

OBJECT OF THE INVENTION

It is an object of the present invention to provide a composition exerting PTDA. Surprisingly, a preparation comprising the 25K IgE-binding factor (25KIgE-bf), also named soluble CD23 (sCD23), and interleukin-1 (IL-1) has PTDA.

Further objects of the invention are the use of said preparation for the stimulation of the maturation of prothymocytes.

DETAILED DESCRIPTION OF THE INVENTION

The invention concerns a pharmaceutical preparation comprising effective amounts of the 25K IgE-bf having the aminoacid sequence with the Sequence Identification (SEQ ID) No. 1 shown in the Sequence Listing, or of a pharmacologically active variant, fragment or derivative thereof and of IL-1 or of a pharmacologically active variant, fragment or derivative thereof as an admixture for the use together or in separate form for sequential use. Said pharmaceutical preparation is hereinafter also referred to as a pharmaceutical preparation according to the invention.

The 25K IgE-bf or a pharmacologically active variant, fragment or derivative there of and IL-1 or a pharmacologically active variant, fragment or derivative thereof are known or can be prepared according to known processes. The 25K IgE-bf, variants, fragments and derivatives thereof and methods for their production are disclosed e.g. in EP-A-0254249 (corresponding to U.S. Pat. No. 5,081,028) and EP-A-0205405 (corresponding to U.S. Pat. No. 4,946,788). IL-1 and methods of producing the same are disclosed e.g. in EP-A-0161901 (corresponding to U.S. Pat. No. 4,762,914; U.S. Pat. No. 4,766,069; and U.S. Pat. No. 5,001,057) and EP-A-0165654 (details of which are reproduced herein after the Examples).

A variant of the 25K IgE-bf is a protein with an altered amino acid sequence in comparison with the amino acid sequence with the SEQ ID No. 1. A variant includes naturally occuring variants, e.g. human allelic variants or variants isolated from non-human mammalian species, e.g. from mouse or monkey. A variant also includes an artificially made variant.

25K IgE-bf or a variant thereof is preferably made by means of recombinant DNA technology, e.g. it is produced by the expression in a heterologous host cell. One or more amino acids may be attached to the N- or C-terminus. To the N-terminus maybe attached e.g. methionine, N-formyl-methionine or N-acetyl-methionine, especially when the expression product is obtained from *Escherichia coli.* An artificially made variant of the IgE-bf of the invention or of a naturally occuring variant thereof includes proteins characterized by the exchange of one or more, about up to 10, of the amino acids of the 25K IgE-bf of the invention or of a naturally occuring variant thereof with one or more of other amino acids.

Within the scope of a fragment of the 25K IgE-bf of the invention are also fragments of variants of said 25K IgE-bf.

A fragment of the 25K IgE-bf or of a variant thereof is an amino acid chain having at least 10 and up to 173 successive amino acids in a sequence corresponding to the invention or to the sequence of a variant thereof. Different or identical fragments may be linked covalently by peptide bonds.

Fragments of the 25K IgE-bf are in particular those of the group consisting of polypeptides starting with anyone of amino acids 2, 3, 4, 5, 6, 7, 8, 9, 10, 11, 12, or 13 and ending with any of the amino acids 135 to 174 of the amino acid sequence with the SEQ ID No. 1. A preferred fragment is characterized in that it consists of the amino acids 3 to 174. This fragment can be found in addition to the 25K IgE-bf of the invention in supernatants of RPMI 8866 cells, and thus represents a naturally occuring fragment.

Derivatives of the 25K IgE-bf or of a variant thereof are such where functional groups, such as amino, hydroxyl, mercapto or carboxyl groups, are derivatized, e.g. glycosylated, acylated, amidated or esterified, respectively. In glycosylated derivatives an oligosaccharide is usually linked to asparagine, serine, threonine and/orlysine. Acylated derivatives are especially acylated by a naturally occuring organic or inorganic acid, e.g. acetic acid, phosphoric acid or sulfuric acid. Usually the N-terminal amino group or hydroxy groups, especially of tyrosine or serine are acylated. Esters are those of naturally occuring alcohols, e.g. methanol or ethanol.

Further derivatives are salts, especially pharmaceutically acceptable salts, for example metal salts, such as alkali metal and alkaline earth metal salts, e.g. sodium, potassium, magnesium, calcium or zinc salts, or ammonium salts formed with ammonia or a suitable organic amine, such as a lower alkylamine, e.g. triethylamine, hydroxy-lower alkylamine, e.g. 2-hydroxyethylamine, and the like.

The term derivative according to the present invention includes also derivatives of a variant or a fragment of the 25K IgE-bf of the invention.

A pharmacologically active variant, fragment or derivative of the 25K IgE-bf has a measurable stimulating influence on the maturation rate of prothymocytes in combination with IL-1 or a pharmacologically active variant, fragment or derivative thereof.

Most preferred is a pharmaceutical preparation comprising the human 25K IgE-bf having the amino acid sequence with the SEQ ID No. 1.

The term IL-1 comprises IL-1 purified from the supernatant of mammalian cells which naturally produce IL-1, e.g. from monocytes, optionally after stimulating the IL-1 production in such cells. IL-1 may be derived from different species, e.g. from human, monkey or mouse, preferentially from human. IL-1 also comprises recombinant IL-1, e.g. recombinant IL-1α or recombinant IL-1β, produced e.g. in $E.\ coli$ or mammalian cells.

The meaning of a derivative of IL-1 is in accordance with the meaning of a derivative of the 25K IgE-bf given hereinbefore. Included within the scope of the present invention are also derivatives of variants or fragments of IL-1.

A pharmacologically active variant, fragment or derivative of IL-1 has a measurable stimulating influence on the maturation rate of prothymocytesin combination with the 25K IgE-bf or a pharmacologically active variant, fragment or derivative thereof.

A pharmaceutical preparation according to the invention has a stimulating influence on the maturation rate of prothymocytes. It comprises effective amounts of the 25K IgE-bf or of a pharmacologically active variant, fragment or derivative thereof and of IL-1 or of a pharmacologically active variant fragment or derivative thereof appropriate to stimulate the maturation of prothymocytes.

Effective amounts of active ingredients of a pharmaceutical preparation according to the invention comprise a ratio of about 50 units of IL-1 or of an equivalent amount of a pharmacologically active variant, fragment or derivative thereof to about 0.25 up to 125 ng, preferentially 25 up to 100 ng, of 25K IgE-bf or of an equivalent amount of a pharmacologically active variant, fragment or derivative thereof. The active ingredients may be admixed or in separate form.

The invention also concerns the use of a pharmaceutical preparation according to the invention for the stimulation of the maturation of prothymocytes in vitro, e.g. in cell culture, or in vivo, i.e in an organism.

A prothymocyte is a hematopoietic stem cell which is able to maturate after stimulation with appropriate differentiating factors into a mature T lymphocyte. A prothymocyte may be, for example, a mammalian, e.g. mouse, monkey or preferentially human, prothymocyte.

A prothymocyte is characterized, for example, by the presence of the CD7 cell surface marker and by the absence of e.g. the CD2, CD3, CD4 and CD8 cell surface markers Accordingly a prothymocyte according to the invention is in particular a CD7+CD2−CD3−CD4−CD8− cell.

Prothymocyte maturation leads to a T cell which is characterized by the presence of certain cell surface markers which have not been detectable on the prothymocyte. Such markers are e.g. CD2, CD3, CD4, CD8 and TCR. Accordingly, the maturation of a prothymocyte leads to the formation of a CD7+CD2+CD3+TCR+CD4+ and/or CD8+cell.

Methods for the determination of cell surface markers are well known in the art, e.g. indirect immunofluorescence techniques.

A prothymocyte is also a cell having cell surface markers typical for prothymocytes derived from a patient with acute lymphoblastic leukemia.

A prothymocyte and the maturation of prothymocytesto T cells may also be monitored on a functional level. The proliferation of a T cell but not of a prothymocyte can be stimulated with a combination of anti-CD2 or anti-CD3 antibody and IL-2. The proliferation of cells can be determined with conventional methods.

A preferred embodiment of the invention is the use of a pharmaceutical preparation according to the invention for the stimulation of the maturation of CD7+CD2−CD3−CD4−CD8− cells to CD2+CD3+TCR+CD4+ and/or CD8+ cells in vitro, e.g. in cell culture, or in vivo, i.e. in an organism.

Stimulation of the maturation of prothymocytes is, for example, performed by the addition of a pharmaceutical preparation according to the invention to a cell culture comprising prothymocytes in such amount that a final concentration of about 0.25 ng/ml up to about 125 ng/ml, preferentially from about 25ng/ml up to about 100 ng/ml, of the 25K IgE-bf or of an equivalent amount of a pharmacologically active variant, fragment or derivative thereof and a final concentration about 50 U/ml of IL-1 or of a pharmacologically acitve variant, fragment or derivative thereof is achieved.

A cell culture comprising prothymocytes is obtained from tissue comprising said cells, e.g. from bone marrow, lymph nodes, embryonal tissue, blood, thymus or tonsils. Said tissue may be obtained by biopsy and said cell culture may be obtained by homogenisation of the tissue, isolation of lymphatic cells, e.g. by centrifugation in a density gradient, and by cultivation the lymphatic cells in an appropriate culture medium. Methods for isolating and cultivating lymphatic cells are known in the art.

Prothymocytes may be further purified from said lymphatic cells according to conventional methods e.g. by sorting the lymphatic cells on a cell sorter or on a plastic surface to which the adherent cell population attaches. The adherent cell population then may be treated with a specifically cytotoxic combination of antibodies not directed against prothymocytes but against cell surface markers of the other cells in the adherent population, and with complement.

The stimulation of the maturation of prothymocytes can lead to the enlargement of a T cell pool and/or to the diminution of a prothymocyte pool in a cell culture or an organism. After in vitro stimulation of prothymocytes isolated from an organism, the cells can be reinfused or reimplanted into an organism of the same or a closely related species or preferentially into the individuum from which the prothymocytes were isolated.

Accordingly, the present invention concerns also the use of a pharmaceutical preparation of the invention for the stimulation of the maturation of prothymocytes in vitro or in vivo, for example for the enlargement of a T cell pool in vitro, e.g. in cell culture, or in vivo, i.e. in an organism, e.g. for the treatment or prevention of a T cell immunodeficiency. Included within the scope of a T cell immunodeficiency are congenital and acquired T cell immunodeficiencies, e.g. AIDS, T cell immunodeficiencies of elderly patients, of patients after therapeutical immuno. suppression, and of patients with autoimmune diseases or with thymic dysfunctions. Preferred is the use for the treatment of AIDS.

The invention concerns also the use of a pharmaceutical preparation of the invention for the stimulation of the maturation of prothymocytes, for example, for the diminution of a prothymocyte pool in vitro, e.g. in cell culture, or in vivo, i.e. in an organism, e.g. for the treatment or prevention of a lymphoblastic leukemia with prothymocyte features, herein. after also referred to as prothymocyte leukemia.

A prothymocyte leukemia is an acute leukemia which is characterized in that the tumour cell is a prothymocyte, e.g. with a CD7+CD4−CD8− phenotype.

A pharmaceutical preparation according to the invention may be administered to an organism, preferentially a mammalian organism, more preferentially a human, parenterally, for example, intramuscularly, subcutaneously, intravenously, or directly into the tissue in which the formation of T lymphocytes takes place, e.g. into the thymus or bone marrow, usually in dosage unit forms such as ampoules or vials. The amounts of the polypeptides to be administered depends on their specific activities, on the age, weight and general condition of the patient, the type and severity of the disease, the mode of administration and has to be based on the judgement of the physician. In general a dose of between about 10 $\mu$g and about 5000 $\mu$g of each of the 25K IgE-bf of the invention, or a pharmacologically active variant, fragment or derivative thereof and IL-1 or a pharmacologically active variant, fragment or derivative thereof per kg body weight and day may be administered.

In a pharmaceutical preparation according to the invention the active ingredients are present in form of a mixture or in separate form. If the active ingredients are comprised in the pharmaceutical preparation in separate form, they may be administered by separate routes.

A pharmaceutical preparation according to the invention, particularly if used for the treatment or prevention of T cell immunodeficiencies or prothymocyte leukemias, comprises conventional pharmaceutically acceptable carriers that are suitable for parenteral, e.g. intramuscular, subcutaneous or intraperitoneal, administration and that do not deleteriously interact with the active ingredients.

There are suitable vials containing a solid powder, or vials, ampoules and the like containing infusion solutions, preferably aqueous solutions or suspensions, it being possible to prepare these before use, for example from lyophilized preparations that contain the active ingredient alone or together with a carrier, such as mannitol, lactose, glucose, dextrose, albumin and the like. The pharmaceutical preparation maybe sterilized and, if desired, mixed with adjuncts, for example preservatives, stabilisers, emulsifiers, solubilisers, buffers and/or salts, such as 0.9% sodium chloride, for regulating the osmotic pressure. Sterilization can be achieved by sterile filtration through filters of small pore size (0.45 $\mu$m diameter or smaller) after which the preparation can be lyophilized, if desired. Antibiotics may also be added in order to assist in preserving sterility.

A pharmaceutical preparation according to the invention is dispensed in unit dosage forms, for example ampules, comprising 1 to 2000 mg of a pharmaceutically acceptable carrier per unit dosage and about 0.001 to 100 mg, preferably about 0.1 to 50 mg, of each of the active ingredients per unit dosage.

The invention also concerns a process for the manufacture of a pharmaceutical preparation of the invention.

Said process is characterized in that the 25K IgE-bf of the invention or a pharmacologically active variant, fragment or derivative thereof and IL-1 or a pharmacologically active variant, fragment or derivative thereof are admixed with a pharmaceutically acceptable carrier or, if the active ingredients are in separate form in the pharmaceutical preparation, are separately admixed with a pharmaceutically acceptable carrier.

A pharmaceutical composition according to the invention is manufactured according to methods known per se, for example by conventional mixing, dissolving, lyophilizing, freeze-drying and the like processes and contain0.1% to 100%, especially from about 1% to 50% of the active substances.

The invention concerns further a pack comprising a pharmaceutical preparation according to the present invention optionally together with instructions for its use.

In an organism or cell culture which has sufficient IL-1 only the 25K IgE-b for a pharmacologically active variant, fragment or derivative thereof or a pharmaceutical preparation comprising the 25K IgE-b for a pharmacologically active variant, fragment or derivative thereof as the only active ingredient has to be administered to stimulate the maturation of prothymocytes. Likewise, in an organism or cell culture having sufficient 25K IgE-bf, only IL-1 or a pharmacologically active variant, fragment or derivative thereof or a pharmaceutical preparation comprising IL-1 or a pharmacologically active variant, fragment or derivative thereof as the only active ingredient has to be administered to stimulate the maturation of prothymocytes.

As already mentioned above, the stimulation of the maturation of prothymocytes can lead to the enlargement of a T cell pool and/or to the diminution of a prothymocyte pool in vitro, e.g. in a cell culture, or in vivo, i.e. in an organism.

Accordingly, the present invention concerns also the use of the 25K IgE-b for a pharmacologically active variant, fragment or derivative thereof, preferentially of the25K IgE-bf, for the stimulation of the maturation of prothymocytes in a cell culture or in an organism, e.g. mouse, monkey or preferentially in human, having sufficient IL-1, for example for the enlargement of a T cell pool, e.g. for the treatment or prevention of a T cell immunodeficiency, preferentially of AIDS, or for the diminution of a prothymocyte pool, e.g. for the treatment or prevention of a prothymocyte leukemia.

Likewise, the invention concerns the use of IL-1 or a pharmacologically active variant, fragment or derivative thereof for the stimulation of the maturation of prothymocytes in a cell culture or in an organism, e.g. mouse, monkey or preferentially in human, comprising sufficient 25K IgE-bf, for example for the enlargement of a T cell pool, e.g. for the treatment or prevention of a T cell immunodeficiency, preferentially of AIDS, or for the diminution of a prothymocyte pool, e.g. for the treatment or prevention of a prothymocyte leukemia. The meaning of IL-1 and preferred forms thereof is the same as given above.

Another subject of the present invention is the use of the 25K IgE-bf or a pharmacologically active variant, fragment or derivative thereof for the manufacture of a pharmaceutical preparation for the stimulation of the maturation of prothymocytes in vitro, e.g. in a cell culture, or in vivo. i.e. in an organism, e.g. in mouse, monkey or preferentially in human, for example for the enlargement of a T cellpool, e.g. for the treatment or prevention of a T cell immunodeficiency, such as those mentioned hereinbefore, preferentially of AIDS, or for the diminution of a prothymocyte pool, e.g. for the treatment or prevention of a prothymocyte leukemia. The pharmaceutical preparation either contains only the25K IgE-bf or a pharmacologically active variant, fragment or derivative thereof or optionally also IL-1 or a pharmacologically active variant, fragment or derivative thereof as active ingredient. The former type of pharmaceutical preparation is for use in a cell culture or organism having sufficient IL-1.

A subject of the invention is also the use of IL-1 or a pharmacologically active variant, fragment or derivative thereof for the manufacture of a pharmaceutical preparation for the stimulation of the maturation of prothymocytes in vitro. e.g. in a cell culture, or in vivo, i.e. in an organism, e.g. in mouse, monkey or preferentially in human, for example for the enlargement of a T cell pool, e.g. for the treatment or prevention of a T cell immunodeficiency, preferentially of AIDS, or for the diminution of a prothymocyte pool, e.g. for the treatment or prevention of a prothymocyte leukemia. The pharmaceutical preparation either contains only IL-1 or a pharmacologically active variant, fragment or derivative thereof or optionally also the 25K IgE-bf or a pharmacologically active variant, fragment or derivative thereof as active ingredient. The former type of pharmaceutical preparation is for use in a cell culture or organism having sufficient 25K IgE-bf.

ABBREVIATIONS

The abbreviations used hereinbefore and in the examples have the following meanings:
AIDS Acquired Immunodeficiency Syndrome
ALL Acute lymphoblastic leukemia
BFU-E Burst forming Unit-Erythrocytes
CFU-GEMM Colony forming Unit-Granulocytes, Erythrocytes, Monocytes, Megakaryocytes
CFU-GM Colony forming Unit-Granulomonocytes
IL-1 Interleukin-1
rIL-1 recombinant Interleukin-1
IL-2 Interleukin-2
rIL-2 recombinant Interleukin-2
Mab-45-affigel Monoclonal antibody 45-coated affinity gel
MHC Major histocompatibility complex
PBL Peripheral blood lymphocyte
PHA Phytohemaglutinine
PTDA Prothymocytes differentiating activity
TcR T cell receptor

EXPERIMENTAL PART

The following examples serve to illustrate the present invention, however, they should not be construed as a limitation thereof.

| Monoclonal Antibodies (mAbs) | | |
|---|---|---|
| mAb | Antigen | Source, Reference |
| OKT6 | CD1 | Ortho Pharmaceuticals |
| OKT11A | CD2 | Ortho Pharmaceuticals |
| OKT3 | CD3 | Ortho Pharmaceuticals |
| OKT4 | CD4 | Ortho Pharmaceuticals |
| OKT8 | CD8 | Ortho Pharmaceuticals |
| WT31 | CD3/TCR$\alpha\beta$ complex | Becton Dickinson, Grenoble, France |
| RFT2 | CD7 | Ref. 20 |
| IOM2 | CD14 | Immunotech |
| IOB4 | CD19 | Immunotech, Marseille, Lumigny, France |
| IOB6 | CD23, 25K IgE-bf | Immunotech, Marseille, Lumigny, France |
| IOT14 | CD25 | Immunotech, Marseille, Lumigny, France |
| anti-Tigamma A | TCR$\gamma$ | Ref. 21 |
| $\delta$TCS-1 | TCR$\delta$ | T cell Sciences, Cambridge, MA |

CULTIVATION OF LYMPHOCYTES

All lymphocytes are cultured routinely in a density from about $10^6$ cells/ml in MacCoy's 5A (Flow Laboratories) medium modified as described in Robinson et al. (Ref. 18). All media are supplemented with human AB-serum (HS), human AB-plasma (HP) or fetal calf serum (FCS). AB-serum and AB-plasma is obtained from donors with AB blood group. Cultures are incubated at 37° C. in a water satured atmosphere containing 6% $CO_2$.

EXAMPLE 1

Stimulation of the Maturation of Purified CD7+CD2−CD3−CD4−CD8− Cells

Thymocytes are obtained in a manner known per se by teasing thymic fragments (Ref. 17). CD7+CD2−CD3−CD4−CD8− cells are isolated from the thymocytes by adherence on plastic surfaces followed by two cycles of cytotoxic treatment as described by Mossalayi et al. (Ref. 8) with OKT11A, OKT3, OKT4 and OKT8 (Ortho Pharmaceuticals, Raritan, N.J.) and subsequent incubation with complement. The complement used in this work is a serum from 4weeks old rabbits obtained by direct intracardiac puncture. The complement is tested for the absence of nonspecifictoxicity on human T cell precursors. CD7+ cells are then positively selected by application of the CD7+CD2−CD3−CD4−CD8− cells into flasks coated with RFT2A monoclonal antibody (IgM, anti-CD7) as described (Ref. 13). The CD7+CD2−CD3−CD4−CD8− cells are collected and centrifuged at 1250 g for 25 min on a Ficollgradient to eliminate dead cells. CD7+CD2−CD3−CD4−CD8− cells recovered from the Ficoll gradient are about 0.37% of total thymocytes.

The maturation of the CD7+CD2−CD3−CD4−CD8− cells was stimulated by incubating them for 48 h at 37° C. in a water satured atmosphere containing 6% $CO_2$ at a density of $10^6$ cells/ml in MacCoy's 5A medium containing 20% of decomplemented and filtered AB-serum obtained from healthy human and one or a combination of the following factors: Recombinant 25 K IgE-bf having the amino acid sequence with the SEQ ID No.1 in a concentration of 25 ng/ml.

rIL-1β (50 U/ml; Glaxo, Geneva).
rIL-2 (100 U/ml; Glaxo, Geneva).
IOB6 (25 μg/ml; monoclonal antibody, IgG1K).
IOT14 (10μg/ml; monoclonal antibody, IgG2a).

The cells are then harvested at 450 g and the maturation state of the cells is tested by analyzing surface markers of the cells with indirect immunofluorescence technique as described in Ref. (8). Cells harvested before incubation with factors as well as cells incubated in nutrient medium without factors are used as control. The cells are labelled with the following monoclonal antibodies (recognized antigen in brackets): OKT6 (CD1), OKT11A (CD2), OKT3 (CD3), OKT4 (CD4), OKT8 (CD8), WT31 (recognizing CD3/TCRαβ complex), IOT14 (CD25), IOB4 (CD19), RFT2A (CD7), anti-TigammaA, or δTCS-1 (TcRδ). Fluorescein conjugated Anti-mouse F(ab') fragments (Beckton Dickinson) are applied as second antibody (all antibodies and fragments are used in a final dilution of 1/50). The results are shown in Table 1.

described in Ref. (8). Cells harvested before incubation with factors as well as cells incubated in nutrient medium without factors are used as control. The cells are labelled with the following monoclonal antibodies (recognized antigen in brackets): OKT6 (CD1), OKT11A (CD2), OKT3 (CD3), OKT4 (CD4), OKT8 (CD8), WT31 (recognizing CD3/TCRαβ complex), IOT14 (CD25), IOB4 (CD19), RFT2A (CD7), anti-TigammaA, or δTCS-1 (TcRδ). Fluorescein conjugated Anti-mouse F(ab') fragments (Beckton Dickinson) are applied as second antibody (all antibodies and fragments are used in a final dilution of 1/50). The results are shown in Table 1.

EXAMPLE 2

Mitogenic Stimulation of the Cells Derived from Maturation Stimulated CD7+CD2−CD3−CD4−CD8− Cells CD7+CD2−CD3−CD4−CD8− cells are incubated for 24 h in the presence of various factors as described in Example 1. They are then washed in Hank's B lanced Salt Solution (HBSS, Institut Pasteur, Paris, France) and subsequently cultured in McCoy's 5A medium ($10^6$ cells/ml, 37° C., 6% $CO_2$) in the presence of an 1:400 diluted ascites containing anti-$CD2_{I+III}$mAb (Ref. 22). On day 5, 1 mCi $^3$H-Thymidin is added to $5 \cdot 10^4$ cells in a final volume of 0.1 ml for 24 h. Cells are washed in HBSS, filtered on Skatron papers (No. 11731; Suffolk, UK), dissolved in scintillation solution (Pico-Fluor, Packard, Groningen, Netherlands), and radioactive counts are determined using a β Scintillation Counter (Beckman). Average results and standard deviation of four independent series of experiments are given in Table 2. No significant proliferation response of the cells are obtained if the solutions of 25K IgE-bf are preincubated with IOB6-coated sepharose beads (data not shown).

TABLE 2

Proliferative response ($^3$H-Thymidine uptake) of CD7+CD2−CD3−CD4−CD8− cells following in vitro conditioning

| Cells preincubated with: | CPM (× $10^3$)/ $5 \cdot 10^4$ CELLS |
|---|---|
| Non | 2.6 + 1.1* |
| recombinant 25K IgE-bf | 2.4 + 1.2 |
| rIL-1β | 2.8 + 1.4 |
| recombinant 25K IgE-bf + rIL-1β | 12.9 + 3.3 |
| rIL-2 | 3.1 + 1.5 |
| rIL-1β + rIL-2 | 3.7 + 1.8 |
| recombinant 25K IgE-bf + rIL-1β + rIL-2 | 16.2 + 4.0 |
| recombinant 25K IgE-bf + rIL-2 | 3.6 + 0.6 |

*Mean + Standard deviation from 4 experiments, each done in triplicate

TABLE 1

Surface phenotype of purified CD7+ thymocytes before and following 48 h incubation with different factors

| Surface marker | % of fluorescence positive cells | | | | | | | | | | | | |
|---|---|---|---|---|---|---|---|---|---|---|---|---|---|
| | CD1 | CD2 | CD3 | WT31 | CD4 | CD4,8 | CD7 | CD8 | CD14 | CD19 | CD25 | TCRαβ | TCRγδ |
| Before incubation | 1 | 2 | 1 | 1 | 1 | 1 | 92 | 1 | 3 | 1 | 4 | 2 | 0 |
| Following incubation with: | | | | | | | | | | | | | |
| non | 3 | 4 | 3 | 2 | 2 | 2 | 93 | 3 | 1 | 1 | 5 | 2 | 1 |
| rIL-1β | 2 | 4 | 4 | 3 | 1 | 2 | 92 | 1 | 1 | 1 | 8 | ND | ND |
| rIL-2 | 2 | 4 | 3 | 2 | 2 | 0 | 90 | 0 | 0 | 1 | 10 | ND | ND |
| recombinant 25K IgE-bf | 1 | 3 | 2 | 1 | 1 | 1 | 86 | 2 | 2 | 1 | 4 | ND | ND |
| rIL-1β + rIL-2 | 2 | 5 | 3 | 2 | 2 | 2 | 89 | 2 | 1 | 2 | 9 | ND | ND |
| recombinant 25K IgE-bf + rIL-2 | 3 | 4 | 4 | 3 | 3 | 1 | 93 | 2 | 3 | 1 | 11 | ND | ND |
| recombinant 25K IgE-bf + rIL-1β | 6 | 53 | 45 | 39 | 23 | 7 | 95 | 37 | 2 | 0 | 34 | 4 | 3 |
| recombinant 25K IgE-bf + rIL-1β + rIL-2 | 7 | 59 | 51 | 39 | 21 | 8 | 97 | 33 | 1 | 1 | 33 | ND | ND |
| recombinant 25K IgE-bf + rIL-1β + IOB6 | 4 | 7 | 5 | 2 | 3 | 3 | 83 | 4 | 2 | 2 | 7 | ND | ND |

ND: not done

EXAMPLE 3

Dose Dependent Mitogenic Stimulation and Maturation of CD7+CD2−CD3−CD4−CD8− Cells CD7+CD2−CD3−CD4−CD8− cells are cultured for 48 h in McCoy's 5A medium ($10^6$ cells/ml, 37° C., 6% $CO_2$) in the presence of a constant rIL1$\beta$ concentration (50 U/ml) and various concentrations of recombinant 25K IgE-bf. The cells are then harvested and washed. The percentage of CD7$^{30}$ prothymocytes acquiring both CD2 and CD3 expression is then determined by indirect immunofluorescence technique with OKT11 (anti-CD2) and OKT3 (anti-CD3) and with rabbit anti-mouse F(ab')$_2$ as second antibody (all antibodies and fragments are used in a final dilution of 1:50). In a parallel experiment the proliferative response of the cells is determined according to Example 2. The results are shown in Table 3.

TABLE 3

Proliferative response ($^3$H-Thymidine uptake) and expression of the cell surface markers CD2 and CD3 in CD7+CD2−CD3−CD4−CD8− cells following incubation in the presence of various concentrations of recombinant 25K IgE-bf

| recombinant 25K IgE-bf (ng/ml) | CD2+CD3+ cells (%)* | Growth responses (CPM × $10^3$)** |
|---|---|---|
| 0 | 7 | 1.2 |
| 0.05 | 7 | 1.3 |
| 0.25 | 17 | 1.8 |
| 2.5 | 30 | 2.6 |
| 25 | 65 | 6.8 |
| 50 | 63 | 6.6 |
| 75 | 59 | 6.2 |
| 100 | 55 | ND |
| 125 | 21 | 2.8 |
| 250 | 6 | 0.8 |

*Mean from 2 experiments, standard deviation <10%
**mean from 2 experiments, standard deviation <25%
ND = Not done.

EXAMPLE 4

Synergistic Effect of 25K IgE-bf and rIL-1$\beta$ on Cloning Capacity of Cells Derived from Maturation Induced CD7+CD2−CD3−CD4−CD8− Cells CD7+CD2−CD3−CD4−CD8− cells are incubated in McCoy's 5A medium ($10^6$ cells/ml, 37° C., 6% $CO_2$) for 48 hours in the presence of 25 ng/ml 25K IgE-bf, 25 μg/ml IOB6, 50 U/mL rIL-1$\beta$, and/or 1000 U/ml rIL-2. IOB4 was used in a concentration of 25 μg/ml as isotype-matched control for IOB6 and had no inhibitory influence on the 25K IgE-bf effect.

The cells are then washed in HBSS and cultured in limiting dilutions as described by Mossalayi et al. (Ref. 8) in the presence of anti-CD2$_{I+III}$ (1:400 ascite, Ref. 22) and 50 U/ml rIL-2. $10^4$ irradiated (2500 rads) autologous CD2− cells are also added per culture. Cloning frequencies are evaluated as described by Porter and Berry (Ref. 23) by scoring positive versus negative wells on day 10 after culturing. Results are shown in Table 4.

TABLE 4

Synergistic effect of recombinant 25K IgE-bf and rIL-1$\beta$ on the cloning capacity of cells derived from maturation induced CD7+CD2−CD3−CD4−CD8− cells

| CELLS PRETREATED WITH: | CLONING FREQUENCY MEAN* | RANGE* |
|---|---|---|
| non | 1/184 | 1/95–1/264 |
| rIL-1$\beta$ | 1/123 | 1/69–1/168 |
| recombinant 25K IgE-bf | 1/145 | 1/119–1/209 |
| recombinant 25K IgE-bf + rIL-1$\beta$ | 1/2.6 | 1/1.8–1/3.6 |
| recombinant 25K IgE-bf + rIL-1$\beta$ + rIL-2 | 1/2.1 | 1/1.6–1/3.2 |
| recombinant 25K IgE-bf + rIL-1$\beta$ + rIL-2 + IOB6 | 1/98 | 1/65–1/112 |

*Mean and range of cloning frequencies (positive wells/negative wells) from 4 distinct donors.

REFERENCES

1. Snodgrass, H. R., Kisielow, P., Kiefler, M., Steinmetz, M. & von Boehmer, H. Nature 313, 592–595 (1985).
2. Raulet, D. H., Garman, R. D., Saito, H. & Tonegawa, S. Nature 314, 103–107 (1985).
3. Born, W., Yague, J., Palmer, E., Kappler, J. & Marrack, P. Proc. Nat. Acad. Sci. U.S.A. 82, 2925–2929 (1985).
4. Ceredig, R., Dialynas, D. P., Fitch, F. W. & MacDonald, H. R. J. Exp. Med. 158, 1654–1671 (1983).
5. Marrack, P. et al. Cell 53, 627–634 (1988).
6. Sia Teh, H. et al. Nature 335, 229–233 (1988).
7. Furley et al. Cell 46, 75–87 (1986).
8. Mossalayi, M. D. et al. Blood, 71, 1281–1287 (1988).
9. Haynes, B. F., Martin, M. E., Key, H. & Kurtzberg, J. J. Exp. Med. 168, 1061–1080 (1988).
10. Kurtzberg, J. et al. Blood 73, 381–390 (1989).
11. Toribio, M. L. et al. J. Exp. Med. 168, 2231–2249 (1988).
12. Rock, K. L. & Benacerraf, B. J. Immunol. 132, 1654–1662 (1984).
13. Mossalayi, M. D. et al. J. Immunol. 134, 2400–2404 (1985).
14. Lecron, J. C. et al. Exp. Hematol. 17, 785–790 (1989).
15. Jurgenson, C. H., Ambrus, J. L. & Fauci, A. S. J. Immunol. 136, 4542–4547 (1986).
16. Taira, S., Matsui, M., Hayakama, K., Yokoyama, T. & Nariuchi, H. J. Immunol. 139, 2957–2964 (1987).
17. Dallol, A. H. et al., Exp. Hematol. 17, 774–778 (1989)
18. Robinson, W. A. (1971) In vitro cell culture of hemopoietic cells. In: Dicke, K. A., and Beckum, V. (eds.). Rijkwijk.
19. Mossalayi et al., Tissue Antigen 33, 100 (1989)
20. Campana, D. et al., J. Immunol. 142, 57–66 (1989)
21. Faure, F. et al., J. Immunol. 141, 3357–60 (1988).
22. Huet, S. et al., Proc. Natl. Acad. Sci USA 84, 7222–26 (1987).
23. Porter, E. H. and Berry, R. J. Br. J. Cancer 17, 583–89 (1963).

PREPARATION OF IL-1

Crude preparations of IL-1 are prepared from peripheral blood leukocytes. The leukocytes are separated from whole blood by well known techniques, such as by centrifugation over a volume of Ficoll/Hyp que solution. The leukocytes removed from the blood are cultured in vitro in a culture medium containing an appropriate stimulating agent to induce IL-1 secretion. After an optimum culture period, the supernatant is harvested by centrifugation and stored until used.

Rather than being obtained from leukocytes removed from whole blood, IL-1 can alternatively be prepared from monocytes derived from any monocyte rich source. Such monocyte sources include monocytic leukemic spleen cells, lymph cells and alevolar macrophages.

The medium used to culture the peripheral blood leukocytes may consist of commercially available media, such as Eagle's Minimum Essential Medium ("MEM") or Roswell Park Memorial Institute ("RPMI") medium. Additives, which may be individually or in combination added to the culture medium, include glutamine, HEPES buffer and various antibiotics, such as gentamycin, penicillin and streptomycin. In the past, serum also has been commonly used as an additive. However, applicants have discovered that in the procedures of the present invention, purification of IL-1 from the culture supernatant is facilitated if serum is not used in the culture. Although not employing serum has been found to result in a three-to-five fold reduction in the quantity of IL-1 produced in culture, the absence of serum also results in a 100-fold reduction in total protein produced, which lessens the complications involved in the purification of the IL-1.

Preferable stimulating agents used in conjunction with the present invention include *Staphylococcus aureus* or lipopolysaccharide ("LPS") extracted from *Excherichia coli* ("*E. coli*"). In addition, phorbol esters, such as phorbal myristrate 13-acetate, may be employed as a stimulating agent.

The process of culturing the leukocytes to induce secretion of IL-1 may be carried out in various environmental conditions. Preferably, however, the cultures are maintained in the temperature range of approximately 35°-38° C. in a humidified atmosphere of approximately 5-10% $CO_2$ in air. The quantity of IL-1 released by stimulation of peripheral blood leukocytes with an activating agent varies with time. Applicants have found that optimum levels of IL-1 expression are reached at approximately 24-72 hours after stimulation.

ASSAYS/ANALYSIS

A thymocyte proliferation assay, an IL-1 conversion assay and a protein assay are employed in conjunction with the present invention to monitor the IL-1 activity level and the protein content of the samples during the purification, cloning and IL-1 expression procedures of the present invention. Also, sodium dodecyl sulfate-polyacrylamide gel electrophoresis ("SDS-PAGE") and two-dimensional gel electrophoresis are used to analyze the IL-1 activity during the purification process.

THYMOCYTE PROLIFERATION ASSAY

This assay involves ascertaining the capacity of a sample of IL-1 to induce proliferation of thymocytes derived from CD-1 mice. In this assay, approximately $1 \times 10^6$ thymocytes obtained from 10 to 12 week old CD-1 mice (Charles River Breeding Laboratories, Wilmington, Mass.) are seeded in round bottom microplate wells (Corning Plastics, Corning, N.Y.) in the presence of three-fold serial dilutions of IL-1 containing samples. The thymocytes are cultured in 150 microliters ("ul") of MEM containing 50 units/milliliter ("U/ml") penicillin, 50 micrograms/milliliter ("ug/ml") streptomycin, 2 millimolar ("mM") glutamine, 0.2 mM gentamycin, 10 mM HEPES buffer, (jointly referred to as "Supplemented MEM"), pH 7.4, together with 3% v/v human serum and $10^{-5}$ molar ("M") 2-mercaptoethanol. The samples are cultured for 72 hours at 37° C. in an atmosphere of 5% $CO_2$ in air. Thereafter the cultures are pulsed for approximately 4 hours with 0.5 microcuries ("uCi") of triturated thymodine ("$^3$H-Tdr"), (New England Nuclear, Boston, Mass., 2 Ci/mM specific activity), after which the cultures are harvested onto glass fiber filter strips, for instance with the aid of a multiple-automated sample harvester. $^3$H-Tdr incorporation is then measured by liquid scintillation counting. Details of this procedure are disclosed in Gillis et al., 120 *J. Immunol.* 2027 (1978).

By this thymocyte proliferation assay procedure, only the CD-1 thymocytes cultured in the presence of IL-1 incorporate $^3$H-Tdr in a dose dependent manner. CD-1 cells cultured in the absence of IL-1 incorporate only background levels of $^3$H-Tdr. IL-1 activity is calculated from the linear portion of the $^3$H-Tdr incorporation data in a manner similar to the procedure used by Gillis et al., supra, for determining interleukin-2 acidity. Units of IL-1 activity are determined as the reciprocal dilution of a sample which genetes 50% of maximal thymocyte. $^3$H-Tdr incorporation as compared to a laboratory standard. For example, if a sample generates 50% of maximal thymocyte $^3$H-Tdr incorporation at a dilution of 1:15, then one unit ("U") of IL-1 is found in 1/15 of the 150 ul assay volume, or 10 ul is said to contain one U of activity. The total sample would, therefore, contain 100 U [1,000 (ul/ml) 10 ul (per U)] of IL-1 activity/ml. See Gillis et al., supra.

IL-1 CONVERSION ASSAY

A second alternative assay for IL-1 activity may be employed which takes advantage of the fact that IL-1 was found by applicants to convert an interleukin 2 ("IL-2") nonproducer murine tumor cell line, LBRM-33-145, to an IL-2 producer. In this assay LBRM-33-1A5 cells, ATCC No. CRL-8079, are inactivated by addition of 50 ug/ml of mitomycin C and incubated for 1 hour at 37° C. 100 ul of the inactivated LBRM-33-1A5 cells ($5 \times 10^5$ cells/ml) are cultured in 96-well flat-bottomed plates in the presence of an equal volume of the mitogen, phytohemagglutinin ("PHA") (1% final concentration) together with serial dilutions of IL-1 containing fluid samples. After 6-24 hours, the existance of IL-2 activity, generated by IL-1 triggered, mitomycin C-inhibited LBRM-33-1A5 cells (and thus IL-1 activity), is directly ascertained by adding 50 ul of IL-2 dependent CTLL-2 cells ($8 \times 10^4$ cells/ml). The microwell cultures are then incubated for 20 additional hours followed by a 4 hour pulse with 0.5 uCi of $^3$H-Tdr (New England Nuclear, Boston, Mass., 2 Ci/mM specific activity). Thereafter, the thymidine-pulsed cultures are harvested onto glass fiber filter strips with the aid of a multiple automated sample harvester (MASH II; Microbioloical Associates, Bethesda, Md.). $^3$H-Tdr incorporation is measured by liquid scintillation counting. Details of this procedure are set forth in Gillis et al. supra, and in U.S. Pat. No. 4,411,992. In this assay, only the CTLL-2 cells cultured in the presence of IL-2 incorporate $^3$H-Tdr in a dose dependent manner. CTLL-2 cells cultured in the absence of IL-2 (and thus IL-1) incorporate only background levels of $^3$H-Tdr. This "conversion" assay has the advantage of being quicker (completion within 24 hours) and approximately 1000 to 10,000 times more sensitive than the above-discussed thymocyte proliferation assay. Nevertheless, both the "conversion" and "proliferation" assays may be employed in conjunction with the present invention.

PROTEIN ASSAY

The protein content of the purification samples is determined by Biorad protein assay which is commercially available from Biorad, Richmond, Calif. This assay employs bovine serum albumin as a standard. The principles and details of this assay are discussed in Bradford, 72 *Anal. Biochem.* 248 (1976).

GEL ELECTROPHORESIS

The culture supernatant and chromatography column fractions are analyzed by SDS-PAGE to monitor the purification procedures of the present invention. This assay is conducted according to the gel stacking procedure of Laemmli, 227 *Nature (London)* 680 (1970). The assay employs 0.75 mm SDS slab gels using a 10-20% gradient of polyacrylamide gel. The gels are run at a constant 30 mA current. The resulting gel samples are silver stained, such as by the method described in Oakley et al., 105 *Anal. Biochem.* 361 (1980).

The particular assay samples that contain a high salt concentration are initially dialyzed against 0.001% SDS in 0.1 mM $NH_4HCO_3$ and then dried under a vacuum. The dried residue is dissolved in a reducing buffer (2% SDS), 1% 2-mercaptoethanol prior to the SDS-PAGE process.

TWO-DIMENSIONAL POLYACRYLAMIDE GEL ELECTROPHORESIS

After completion of the purification procedures of the present invention, the IL-1 is analyzed by two-dimensional polyacrylamide gel electrophoresis by the method described in Sammons et al., 2 *Electrophoresis* 135 (1981). In the procedure lyophilized IL-1 samples are resuspended in 20 ul of SDS solubiliation buffer composed of 1% (w/v) cyclohexy-laminoethane, 2% (w/v) SDS, 2% 2-merceptoethanol, 10% glycerol in water. The samples are heated to 100° C. for 10 minutes. After two hours of prefocusing, samples (solubilized for 10 min. in SDS at 100° C.) are applied to the first dimension gel and focused for 20 hours at a constant voltage of 600 volts. The first dimension focusing gels are scanned directly with a pH gradient gel scanner. Thereafter the gels are rinsed in equalization buffer [9.3% (v/v) glycerol; 50% (v/v) Tris-SDS buffer (30 g Tris, 2 g. DSD per liter, adjusted to pH 6.8 with concentrated HC); 1% (w/v) SDS; 0.8% (v/v) 2-mercaptoethanol in water] for 2 minutes, placed on top of the second dimension gel and then covered with low temperature melting agarose. The second dimension electrophoresis (10-20% linear gradient of acrylamide) is conducted at a constant current of 40 mA/gel until the dye front reaches the bottom of the gel. After fixation in 50% (v/v) ethanol and 10% (v/v) glacial acetic acid, the gels are stained by color silver nitrate method of Sammons et al., supra.

PURIFICATION OF IL-1

The supernatant resulting from the blood leukocyte culture as prepared by the above procedure is purified by cation exchange chromatography, anion exchange chromatography, and affinity chromatography employing a dye-ligand coupled to a column matrix. All chromatography fractions are assayed for IL-1 activity and protein concentration. Where appropriate, pH and conductivity are measured. Following each chromatography step, samples are analyzed by SDS-PAGE. In addition, after completion of the affinity chromatography procedure, active fractions are analyzed by two-dimensional polyacrylamide gel electrophoresis as discussed above.

A suitable column for the cation exchange chromatography process is composed of sulfopropyl Sephadex C-25 (Pharmacia Fine Chemicals, Piscataway, N.J.). Preferably, the column is equilibrated with buffer prior to application of the IL-1 sample and then washed with the same or different buffer after the IL-1 sample has been applied to the column to remove nonbound protein without elution of IL-1 activity. Elution of the IL-1 from the column is carried out with a buffered elutant of sufficient pH to disassociate the IL-1 from the column.

The pooled active fractions from the cation exchange chromatography procedure are further purified by anion exchange chromatography. Applicants have found that a suitable column material for this purpose is DEAE-Sephacel. The DEAE-Sephacel column is equilibrated with a buffer and the sample concentrate applied to the column. Elution is initially carried out with the starting buffer and then subsequently with a linear salt gradient in the same buffer. Fractions are collected and analyzed as discussed above.

The IL-1 in the pooled active fractions from the DEAE-Sephacel column is further purified by affinity column chromatography employing a synthetic triazinyl textile dye-ligand coupled to a support matrix. Various dye colors may be employed including blue or red. The dye is coupled to an appropriate column matrix composed of, for instance, agarose, polyacrylamide, cellulose or silica-based inorganic materials via an ether linkage to the triazine ring or alternatively via a primary amine or an anthraquinone group of the dye. Rather than being bound directly to a support matrix, the dye can be bound to high molecular weight dextran with the dextran then immobilized to a column matrix. Partial chemical structures of blue and red dye-ligands coupled to a matrix are shown in FIGS. 1 and 2, respectively. It is to be understood that these dye structures can be modified to form analogs, for instance by exchanging the positions of the sulfonated anthraquinone group relative to the triazine ring or by substituting a sulfonate slat for the sulfonic acid substituents. See Fulton, *Dye-Ligand Chromatography*, Lexington, Mass.: Studio 6, Inc. (1980).

Prior to applying the IL-1 containing fractions purified over SP-Sephadex and DEAE-Sephacel to the dye-ligand column, it may be necessary to lower the ionic strength of the pooled active fractions. Also, the presence of a divalent cation, such as $Mg^{++}$ or $Ca^{++}$, may enhance the binding of IL-1 to the dye-ligand. The column is equilibrated with an appropriate buffer, such as Tris-HCL, and then pooled DEAE fractions containing IL-1 activity are applied to the column. Thereafter, the column is washed with the same starting buffer and then elution is carried out with a linear salt gradient in the same buffer or a specific soluble ligand. Fractions are collected and analyzed as discussed above.

Applicants have discovered that red triazinyl textile dye, when used under the stated column conditions, is especially highly specific for binding IL-1. A commercial brand of this red dye corresponding to FIG. 2 is "Procion" red (reactive red 120) (Imperial Chemical Industries). Applicants have also discovered that blue triazinyl textile dye when used under the stated column conditions is also highly specific for binding IL-1, i.e. approximately 80% as specific as red triazinyl textile dye. A commercial brand of blue dye is Cibacron® Blue 36A (Ciba A G).

By the aforementioned purification process, applicants have purified human IL-1 protein to greater than 99% purity while maintaining a high yield of about 53% from the starting supernatant. By the above-described assay procedures, applicants have determined that human IL-1 is composed of a singular molecular weight specie of approximately 17,500 daltons molecular weight. This molecular weight is substantially heavier than previously reported for either human or murine IL-1. Moreover, contrary to reports of other observers, no other molecular weight species of IL-1 were found by applicants. See Lachman, supra; Togawa et al., supra; Mizel et al., supra; and Blyden et al., supra. Nevertheless, because of the high yields of IL-1 experienced by applicants by use of the present invention, it is unlikely that any significant amounts of other lower modular weight IL-1 species were lost during the aforementioned purification process. The true molecular weight for homogeneous human IL-1 is therefore 17,500 daltons.

AMINO ACID COMPOSITION ANALYSIS

In addition to making possible the biological study of IL-1 free from contamination by other proteins, the ability to prepare homogeneous IL-1 has enabled applicants to determine the amino acid composition of the IL-1 molecule. This information may be employed to assist in the cloning of the IL-1 gene and the production of large quantities of pure IL-1 for clinical trials and ultimately for clinical use.

Samples of purified IL-1 from the affinity chromatography procedure are analyzed for amino acid composition with an automated analyzer using ninhydrin detection. Observed peaks are integrated with commercially available recording integrator. Through this technique, applicants have determined the amino acid composition of the IL-1 molecule as summarized in Table I in Example 4, below.

Since the amino acid residue cysteine (Cys) is unstable to hydrolysis, this residue is not detected by automated ninhydrin analysis. The presence of the Cys residue was detected by the amino acid sequencing analysis, discussed below. Also, automated ninhydrin analysis does not distinguish aspartic acid residue from asparagine residues nor does it distinguish glutamic acid residues form glutamine residues. However, from amino acid sequencing analysis, discussed below, an asparagine residue and six glutamine residues were detected in a N-terminal portion of the IL-1 molecule (consisting of 42 amino acid residues). Thus, in Table I the aspartic acid and asparagine residues are listed together, as are the glutamic acid and glutamine residues.

AMINO ACID SEQUENCE ANALYSIS OF N-TERMINAL PORTION OF IL-1 MOLECULE

Applicants have also investigated the amino acid sequence of the IL-1 molecule. Applicants have discovered that in the purified IL-1 prepared by the procedures set forth above, the N-terminus of this molecule is partially blocked. As such, the molecule is not readily amenable to the chemical analysis technique employed in automated amino acid sequencing apparatuses, and thus the amino acid sequence of the entire molecule could not be determined by standard analysis procedures. As a result, applicants employed a combination of two techniques to analyze the sequence of the N-terminal portion of the protein molecule.

As a first technique applicants subjected a rather large sample of over 11 ug of IL-1, as purified to homogeneity by the aforediscussed methods, to amino terminal Edman degradation sequence analysis with an automated sequencing apparatus. By this technique the first 20 residues of the N-terminal portion of the IL-1 molecule was found to be composed of the following sequence: $NH_2$-Ala-Pro-Val-Arg-Ser-Leu-Asn-Cys-Thr-Leu-Arg-Asp-Ser-Gln-Gln-Lys-Ser-Leu-Val-Met.

The 8th residue was deduced to be Cys. In the eighth cycle of the automated sequencing procedure no other residue was obtained in high yield, which points to the conclusion that the eighth residue is composed of Cys (which is not affirmatively detected by Edman degradation), a glycosylated threonine residue or a glycosylated serine (Ser) residue. These later two possibilities were eliminated since, as discussed below, no glucosamine or galactosamine was observed from the amino acid composition analysis. This leads to the conclusion that the 8th residue is composed of Cys.

As a second amino acid sequence analysis technique, applicants fractionated the molecule at the argine residues with the enzyme trypsin. To prevent the trypsin from also cleaving the IL-1 molecule at the lysine sites, the side chains of the lysine molecule were protected with a specific blocking agent. Preferably, the trypsin is treated with L-1-tosylamino-S-phenylethylchloromethylketone ("TPCK") to deactivate other contaminating enzymes, such as chymotrypsin, that may also be present, thereby minimizing the possibility that the IL-1 protein will be cleaved at other residues. It is to be understood that rather than employing trypsin, other enzymes may be used to cleave the IL-1 molecules at other residue sites.

After cleavage of the IL-1 molecule, the resulting peptides were separated on the basis of hydrophobocity of HPLC procedures. The HPLC technique used in the present invention preferably employs a reversed phase, octadecyl bonded silica column having a pore size sufficiently large to be optimally utilized with the proteineaceous IL-1 peptides, i.e., a pore size of at least 300 A.

Suitable reversed phase HPLC columns for use in the practice of the present invention are articles of commerce. A preferred column for this purpose is the Vydac 218 TP reversed phase column commercially available from Separations Group, Hesperia, Calif. This column consists of octadecyl silane groups covalently bonded by means of a siloxane (silican-oxygen-silicaon) bond to the surface of the 300 A pore diameter silica gel which has been classified to a mean particle size of 5 microns. It is to be understood that the use of other reversed phase columns is within the scope of the present invention.

The IL-1 peptides that are bonded to the octadecyl column are eluted by the use of a linear gradient of acetonitrile. A preferred gradient for this purpose is a 0 to 95% (v/v) acetonitrile gradient in trifluoroacetic acid (TFA), pH 2.0.

The eluted peptides can be conveniently monitored with commercially available detection systems. For example, the relative protein concentration in the fractions eluted from the HPLC columns can be determined by measuring absorbance of the eluted material with an automated ultraviolet light spectrophotometer, at 230 nanometers wavelength. A suitable automated ultraviolet light absorbance detection apparatus is available from Waters Associates, Millford, Me. Alternatively, protein elution can be monitored with an automated fluorescence detection system, as described by Stein and Moschera, 78 *Meth. Enzymol.* 435 (1981).

The eluted HPLC fractions are analyzed in sequence by gel electrophoresis, discussed above, to determine the number of peptides contained in each of the HPLC fractions. Thereafter, the peptides are concentrated in vacuo and then analyzed for amino acid sequence. This is preferably carried out with an automated sequencing apparatus, which are articles of commerce. Through this technique, applicants have discovered that a major portion of the Il-1 molecule near the N-terminal portion of the human IL-1 molecule is composed of the following sequence of molecule residues: -Ser-Leu-Val-Met-Ser-Gly-Pro-Tyr-Glu-Leu-Lys-Ala-Leu-His-Leu-Gln-Gly-Gln-Asp-Met-Glu-Gln-Gln-Val-Val-Phe.

The first four residues of the amino terminal portion of this amino acid fragment corresponds with the last four residues of the C-terminal portion of the sequence determined above by automated Edman degradation technique, thus leading to the conclusion that the first 42 residues of the N-terminal portion of the Il-1 molecule is composed of the following sequence: $NH_2$-Ala-Pro-Val-Arg-Ser-Leu-Asn-Cys-Thr-Leu-Arg-Asp-Ser-Gln-Gln-Lys-Ser-Leu-Val-Met-Ser-Gly-Pro-Tyr-Glu-Leu-Lys-Ala-Leu-His-Leu-Gln-Gly-Gln-Asp-Met-Glu-Gln-Gln-Val-Val-Phe.

PREPARATION OF RNA FROM HUMAN IL-1 PRODUCING CELLS

Total RNA from human IL-1-producing cells is extracted by standard methods, such as disclosed by Chirgwin et al., 18 *Biochemistry* 5294 (1979), and Maniatis et al., *Molecular Cloning, a Laboratory Manual*, Cold Spring Harbor Laboratory, Cold Spring Harbor, N.Y. (1982).

As is well known, when extracting RNA from cells, it is important to minimize ribonuclease ("RNase") activity during the initial stages of extraction. One manner in which this is accomplished is to denature the cellular protein, including the RNase, at a rate that exceeds the rate of RNA hydrolysis by RNase. In the procedures of Chirgwin et al., supra, and Maniatis et al., supra at 196, the is carried out by use of guanidinium thiocyanate, together with a reducing agent, such as 2-mercaptoethanol (to break up the protein disulfide bonds). The RNA is isolated from the protein by standard techniques, such as phenol/chloroform extraction, ethanol precipitation or sedimentation through cesium chloride.

Next, polyadenylated mRNA is separated from the extracted protein. Although, several techniques have been developed to carry out this separation process, one preferred method is to chromatograph the polyadenylated mRNA on oligo (dT)-cellulose as described by Edmonds et al., 68 *Proc. Natl. Acad. Sci.* 1336 (1971); Aviv and Leder, 69 *Proc. Natl. Acad. Sci.* 1408 (1972); and, Maniatis et al., supra at 197. The oligo (dT)-cellulose column is prepared with a loading buffer and then the mRNA applied to the column. Thereafter, the column is initially washed with a buffer solution to remove the unpolyadenylated mRNA, and then the polyadenylated mRNA is eluted from the column with a buffered, low ionic strength eluent. The integrity of the polyadenylated mRNA is verified by gel electrophoresis.

The polyadenylated mRNA is then sized by electrophoresis through methylmercury agarose gel fractions corresponding to different size classes of mRNA and then translated in vitro, by use of standard rabbit reticulocyte lysates technique, such as described by: Pulmiter, 248 *J. Biol. Chem.* 2095 (1973); Pelhan and Jackson, 67 *Eur. J. Biochem.* 246 (1976); and, Lee et al., 253 *J. Biol. Chem.* 3494 (1978). Kits for the rabbit reticulocyte assay are commercially available from many sources, such as from Bethesda Research Laboratories, Gaithersburg, Md. Alternatively, the mRNA translation can be carried out by microinjection of the mRNA into frog *Xeaopus laevis* ("*X. laevis*") oocytes using standard techniques, such as described by Stoma et al., 79 *Meth. Enzym.* 68 (1981). Fluids liberated by either reticulocyte lysate translations, or by mRNA microinjected oocytes are then tested for the presence of IL-1 activity by use of the assays discussed above. mRNA gel fractions which, when translated in vitro gave rise to IL-1 activity, are selected as a source of mRNA for cDNA construction.

In the *X. laevis* oocyte translation procedure, approximately 50 nanoliters ("nl") of mRNA (dissolved in sterile $H_2O$ at a concentration of 0.15–1 mg/ml) is injected into each oocyte. The oocytes are harvested from *X. laevis* (Nasco, Fort Atkinson, Wis.) and incubated in 150 ml of oocyte incubation medium (88 mM NaCl, 1 mM KCl, 2.4 mM $NaHCO_3$, 0.82 mM $MgSO_4 \cdot 7 H_2O$, 0.33 mM Ca $(NO_3)_2 \cdot 4H_2O$, 0.41 mM $CaCl_2 \cdot 6H_2O$, 7.5 mM Tris base, 18 units/ml (11 ug/ml) penicillin G potassium, and 18 ug/ml streptomycin). The final pH of the medium is adjusted to 7.6 with HCl and then sterilized by filtration. After injection, the oocytes are placed in 0.1 ml of fresh oocyte incubation medium and incubated for 18 hours at 23° C. in a 1.5 ul sterile conical polypropylene tube. After incubation, the fluid in which the oocytes were cultured is harvested and tested for the presence of IL-1 activity by use of the assays discussed above.

PREPARATION OF cDNA FROM mRNA

A library of double-stranded cDNA corresponding to the mRNA, as prepared and assayed above, is constructed by know techniques employing the enzyme reverse transcriptase. One such procedure which may be employed in conjunction with the present invention is detailed by Maniatis et al., supra at 230. Briefly, the polyadenylated mRNA is reverse transcribed by using oligo-dT, that has been hybridized to the polyadenylated tail of the mRNA, as a primer for a first cDNA strand. This results in a "hairpin" loop at the 3' end of the initial cDNA strand that serves as an integral primer for the second DNA strand. Next, the second cDNA strand is synthesized using the enzyme DNA polymerase I and the hairpin loop is cleaved by S1 nuclease to produce double-stranded cDNA molecules. The double-stranded cDNA is fractionated by any convenient means to remove the shorter strands, thereby avoiding the needless cloning of small cDNA fractions.

It is to be understood that in accordance with the present invention, alternative standard procedures may be employed to prepare double-stranded cDNA from mRNA. One such alternative technique is disclosed by Land et al., 9 *Nucl. Acids Res.* 2251 (1981). In the Land et al. protocol, the hairpin loop is not used as a primer for the second cDNA strand. Rather, the 3' end of the first cDNA strand is tailed with dCMP residues using terminal deocynucleotidyl transferase ("TdT"). This produces a 3' tail of poly-C residues. Then the synthesis of the second strand is primed by oligo-dG hybridized to the 3' tail. This technique is said to help avoid losing portions of the 5' tail of the second cDNA strand which might occur if the hairpin is cleaved with S1 nuclease, as in the Maniatis et al. protocol.

CLONING OF cDNA

Next, the double-stranded cDNA is inserted within a cloning vector which is used to transform compatible prokaryotic or eukaryotic host cells for replication of the vector. Thereafter, the transformants are identified and plasmid DNA prepared therefrom.

To carry out the present invention, various cloning vectors may be utilized. Although the preference is for a plasmid, the vector may be a bacteriophage or a cosmid. If cloning occurs in mammalian cells, viruses also can be used as vectors.

If a plasmid is employed, it may be obtained from a natural source or artificially synthesized. The particular plasmid chosen should be compatible with the contemplated transformation host, whether a bacteria such as $E.$ $coli$, yeast, or other unicellular microorganism. The plasmid should have the proper origin of replication for the particular host cell to be employed. Also, the plasmid should have a phenotypic property that will enable the transformed host cells to be readily identified and separated from cells that do not undergo transformation. Such phenotypic characteristics can include genes providing resistance to growth inhibiting substances, such as an antibiotic. Plasmids are commercially available that encode genes resistant to various antibiotics, including tetracycline, streptomycin, sulfa drugs, penicillin and ampicillin.

If $E.$ $coli$ is employed as the host cell, many possible cloning plasmids are commercially available which may be used in conjunction with the present invention. A preferred plasmid for performing the present invention is pBR322. This plasmid has been fully sequenced, as set forth in Sutcliffe, 43 *Cold Spring Harbor Symp, Quent. Biol.* 77 (1979). A significant advantage of this plasmid is that it has 11 known unique restriction sites, including the Pst I site in the ampicillin resistant gene. This feature is particularly useful for cloning by the homopolymer tailing method.

If a bacteriophage is used instead of a plasmid, such phages should have substantially the same characteristics noted above for selection of plasmids. This includes the existence of a phenotypic marker and ligatable termini for attachment of foreign genes.

Preferably, in the present invention, the double-stranded cDNA, having blunt ends, is inserted into a plasmid vector by homopolymeric tailing. As is well known in the art, in this technique, complementary homopolymer tracks are added to the strands of the cDNA and to the plasmid DNA. The vector and double-stranded cDNA are then joined together by hydrogen bonding between complementary homopolymeric tails to form open, circular hybrid molecules capable of transforming host cells, such as $E.$ $coli$.

In one procedure for homopolymeric tailing, approximately 50 to 150 dA nucleotide residues are added to the 3' ends of linearized plasmid DNA. A similar number of dT nucleotide residues are added to the 3' ends of the double-stranded cDNA and then the cDNA and plasmid joined together.

In an alternative and preferred method, dG tails are added to the 3' ends of the cloning vector that has been cleaved with an appropriate restriction enzyme. For instance, if the pBR322 plasmid is employed, the restriction enzyme Pst I may be used to digest the plasmid at the ampicillin resistant gene. Complementary dC tails are added to the 3' ends of the double-stranded cDNA prior to insertion of the cDNA segment in the plasmid with an appropriate annealing buffer.

It is to be understood that the double-stranded cDNA may be inserted within plasmid cloning vectors by other various standard methods. One such alternative technique involves attaching synthesized nucleotide linkers to the ends of the cDNA strands by using DNA ligase. The linkers are cleaved with a restriction enzyme to generate cohesive termini for insertion within a plasmid cleaved with the same restriction enzyme. Scheller et al., 196 *Science* 177-180 (1977); Maniatus et al., supra at 219.

The recombinant DNA plasmids, as prepared above, are used to transform host cells. Although the host may be any appropriate prokaryotic or eukaryotic cell, it is preferably a well-defined bacteria, such as $E.$ $coli$ or a yeast strain. Such hosts are readily transformed and capable of rapid growth in culture. Other forms of bacteria, such as salmonella or pneumococcus, may be substituted for $E.$ $coli$. In place of bacteria, other unicellular microorganisms may be employed, for instance, fungi and algae. Whatever host is chosen, it should not contain a restriction enzyme that would cleave the recombinant plasmid.

If $E.$ $coli$ is employed as a host, preferable strains of MM294 and RR1. Protocols for transformation of the MM294 host by a plasmid vector are well known, as set forth in Maniatis et al., supra at 255; and, Hanahan, 166 *J. Mol. Biol.* 557 (1983). Protocols for transformation of the RR1 host by a plasmid vector are also well known as set forth in Bolivar et al., 2 *Gene* 95 (1977) and Peacock et al., 655 *Biochem. Biophys, Acta,* 243 (1981). Other strains of $E.$ $coli$ which also could serve as suitable hosts include DH1 (ATCC No. 33849) and C600. These strains and the MM294 and RR1 strains are widely commercially available.

In transformation protocols, including those disclosed by Maniatis et al., supra, and Hanahan, supra, only a small portion of the host cells are actually transformed, due to limited plasmid uptake by the cells. The cells that have been transformed can be identified by placing the cell culture on agar plates containing suitable growth medium and a phenotypic identifier, such as an antibiotic. Only those cells that have the proper resistance gene (e.g., to the antibiotic) will survive. If the recombinant pBR322 plasmid is used to transform $E.$ $coli$ strain MM294, transformed cells can be identified by using tetracycline as the phenotypic identifier.

PREPARATION OF A SYNTHETIC OLIGONUCLEOTIDE SCREENING PROBE

A radiolabled synthetic oligonucleotide corresponding to part of the N-terminal portion of the amino acid sequence of human IL-1 molecule, as determined above, is used as a probe to screen the cDNA library. The hybridization of the synthetic oligonucleotide probe with plasmid cDNA prepared from the library clones is subsequently identified by autoradiography.

The N-terminal portion of the amino acid composition of IL-1 molecule was determined above as composed of the residues: $NH_2$-Ala-Pro-Val-Arg-Ser-Leu-Asn-Cys-Thr-Leu-Arg-Asp-Ser-Gly-Gln-Lys-Ser-Leu-Val-Met-Ser -Gly-Pro-Tyr-Glu-Leu-Lys-Ala-Leu-His-Leu-Gln-Gly-Gln-Asp-Met-Glu-Gln-Gln-Val. This sequence information is employed as the basis for the synthetic oligonucleotide probe.

Applicants developed a synthetic oligonucleotide from the above amino acid sequence for use as a probe to screen plasmid DNA thought to contain the IL-1 gene. The probe is composed of the following sequence which corresponds to the antisense sequence coded for by the above amino acid sequence downstream from the first Met residue: 5'-AC TTG TTG TTC CAT GTC TTC GCC TTG CAG GTG CAG GGC TTT CAG TTC GTA GGG GCC GGA CAT-3'. This probe has the advantage of being short enough to be easily synthesized, while being long enough to contain sufficient information to be useful as a probe for the IL-1 gene. Although the described oligonucleotide sequence is a preferred composition of the synthetic probe of the present invention, it is to be understood that probes of other compositions corresponding to other segments of N-terminal amino acid sequence of the IL-1 molecule can be employed without departing from the spirit or scope of the present invention.

The synthetic oligonucleotide probes may be chemically synthesized by well-known techniques, such as by phosphodiester or triester methods. The details of the triester synthesis technique are set forth in Sood et al., 4 *Nucl. Acid Res.* 2557 (1977); and, Hirose et al., 28 *Tet. Lett.* 2449 (1978). After synthesis, the oligonucleotide probe is labeled with T4 polynucleotide kinase and $^{32}$P-ATP. A standard protocol from the labeling procedure is set forth in Maniatis et al., supra at 122. Advantageously, the oligonucleotide probes can be synthesized with OH 5' terminal thereby avoiding the phosphatase procedure typically required.

SCREENING OF cDNA LIBRARY

In the screening procedure of the present invention, the transformants are pooled into groups each composed of approximately 2,000 transformants. The replicated plasmids are extracted from the transformants using any one of several well-known techniques, such as by alkaline lysis. Plasmid DNA is prepared by cleaving the plasmids at the Pvu II and Hind III restriction sites, both being unique sites on the hybrid plasmid. The resulting DNA segments are fractionated by electrophoresis on agarose gel and then directly analyzed by Southern blotting as described in Southern, 98 *J. Mol. Biol.* 503 (1975). The DNA that binds to the nitrocellulose filter in the Southern blotting procedure is hybridized with the labeled oligonucleotide probe. The specific DNA fragments that hybridize to the probe are identified by autoradiography.

The particular pool(s) of clones that give a signal following autoradiography are plated out and used in direct bacterial colony hybridization on a nitrocellulose filter with the same above-identified oligonucleotide probes. After completion of the hybridization, the nitrocellulose filter is monitored by autoradiography to identify the largest colony. In the present invention, applicants discovered one such colony. Plasmid DNA designated as IL-1 X-14 is prepared from the particular positive colony identified.

CHARACTERIZATION OF SCREENED cDNA

The plasmid DNA prepared above is characterized by restriction enzyme mapping. Various strategies for restriction enzyme mapping are discussed by Maniatis et al., supra at 374. One standard technique involves the partial digestion of end-labeled fragments of linear DNA. This technique was developed by Smith and Birnstiel, 3 *Nucl. Acids Res.* 2387 (1976). A partial restriction enzyme map of the IL-1 X-14 plasmid in the region of the IL-1 gene is shown in FIG. 3. The distance between restriction sites is given in base pairs ("bp"). The Pst I restriction sites shown in the brackets are those generated by the cloning procedures.

The mapped plasmid cDNA illustrated in FIG. 3 was sequenced using the chain-termination method. This method of nucleotide sequencing was originated by Sanger et al., 70 *Proc. Natl. Acad. Sci.* (USA) 5463 (1977). See also U.S. Pat. No. 4,322,499. Methods for chain-termination sequence determination are set forth in the Amersham Handbook entitled, *M13 Cloning and Sequencing,* Blenheim Crescent, London (1983) (hereinafter "Amersham Handbook"); Messing, 2 *Recombinant DNA Technical Bulletin, NIH Publication No.* 79-99, 2, 43-48 (1979); Norrander et al., 26 *Gene,* 101 (1983); Cerretti et al., 11 *Nucl. Acids Res.* 2599 (1983); and, Biggin et al., 80 *Proc. Natl. Acad. Sci.* (USA) 3963 (1983). M13 filamentous phage are employed as vectors to clone the DNA sequences of interest. These phage vectors provide single-stranded DNA templates which are readily sequenced by chain-termination method, which involves priming a single-stranded template molecule with a short primer strand having a free 3' hydroxyl group and then using DNA polymerase to copy the template strand in a chain extension reaction using all four deoxyribonucleotide triphosphates, i.e., dATP, dCTP, dGTP, and dTTP (collectively referred to as "dNTPs"), with one of them being radiolabeled. In the synthesis reaction, a nucleotide specific chain terminator lacing a 3'-hydroxyl terminus, for instance, a 2',3'dideoxynucleotide triphosphate ("ddNTP"), is used to produce a series of different length chain extensions. The terminator has a normal 5' terminus so that is can be incorporated into a growing DNA chain, but lacks a 3' hydroxyl terminus. Once the terminator has been integrated into the DNA chain, no further deoxynucleotide triphosphates can be added so that a growth of the chain stops. Four separate synthesizing reactions are carried out, each having a ddNTP of one of the four nucleotide dNPTs, i.e., dATP, dCPT, dGTP and dTTP. One of the normal dNTPs is radiolabeled so that the synthesized strands after having been sorted by size on a polyacrylamide gel, can be autoradiographed. The chain extensions from the four reactions are placed side by side in separate gel lanes so that the pattern of the fragments from the autoradiography corresponds to the DNA sequence of the cloned DNA.

The DNA and corresponding amino acid sequences of the plasmid cDNA in FIG. 3, as determined by the above techniques, is illustrated in FIG. 4. the nucleotides are numbered from the beginning of the sequence shown in FIG. 4. The amino acids are numbered beginning from the mature NH$_2$-terminus of the IL-1 protein, i.e., the Ala residue, marked with an arrow, and extending to the Ser residue (No. 153) located adjacent the termination codon TAA. The coding region of the IL-1 gene, extending from the Ala codon to the TAG termination codon, is shown as a box portion in FIG. 3. The restriction enzyme cleaving sites identified in FIG. 3 are also indicated in FIG. 4.

In preparation for the sequencing procedures, the plasmid cDNA section shown in FIG. 3 is digested with various restriction endonucleases and then the resulting DNA fragments cloned into M13 phage vectors to form single stranded DNA templates. A universal primer is used to sequence upstream and downstream from intermediate locations of the sense and antisense strands. Rather than relying on the sequencing results obtained from sequencing the entire length of the fragments with a single chain termination procedure, additional synthetically produced primers are used to initiate the chain termination procedure from other intermediate locations along the lengths of the strands. By this process, both strands of the plasmid cDNA shown in FIG. 3 are sequenced in overlapping fashion, thereby serving to redundantly confirm the sequences.

It is to be understood that rather than employing the chain-termination technique outlined above, other known methods may be utilized to sequence the IL-1 gene without departing from the spirit or scope of the present invention. For instance, the chemical degradation method of Maxam and Gilbert as set forth in 74 *Proc. Nat'l Acad. Sci. (USA)* 560 (1977) can be used.

Amino acid sequence studies of IL-1 prepared as above and purified were conducted according to the method of Stern et al., *Proc. Natl. Acad. Sci. (USA)* 871 (1984). The endopeptidase, cyanogen bromide was used to cleave the IL-1 at the methionine residues and then the resulting fragments analyzed by standard Edman degradation method. By this procedure, applicants have confirmed that the C-terminal of the IL-1 protein is composed of the amino acid sequence: Gln-Phe-Val-Ser-Ser. This establishes that the "natural" IL-1 is not processed by removal of amino acids from this end of the molecule after translation from mRNA. This is important because it is clear that much of the coded protein is removed from the 5' end of the open reading frame of the IL-1 gene during the maturation of IL-1 from its precursor.

EXPRESSION OF FUNCTIONAL IL-1 FROM cDNA CLONE

To determine whether the cDNA coding region of the IL-1 X-14 clone could encode functional IL-1, the clone is expressed in a prokaryotic/eukaryotic host system. A hybrid cDNA fragment containing the coding region of the IL-1 X-14 clone is inserted into a shuttle expression vector having two sets of replication sequences, a first sequence for amplification of the vector in prokaryotic host cells, and a second sequence for high level expression of the foreign structural protein, i.e., IL-1, in eukaryotic host cells. The transformed eukaryotic host cells are harvested and assayed for expression of mature IL-1 by use of the above detailed thymocyte proliferation assay and IL-2 conversion assay.

Various types of shuttle vectors have been developed. A common type includes an origin of replication and promoter sequences that signal DNA replication in prokaryotic cells, typically *E. coli* and a comparable origin of replication and promoter sequences that signal DNA replication in eukaryotic cells, most commonly yeast cells. The shuttle vector also includes a phenotypic marker, such as a drug resistant gene, for selection of the transformed prokaryotic cells. The shuttle vector has a comparable phenotypic marker change for selection of transformed eukaryotic cells. Ideally, for high level expression of IL-1, all protein coding sequences are removed from the eukaryotic promoter sequence to avoid expression of an undesired protein. Also, to this end, a natural or synthetic initiator codon sequence, i.e., ATG, is attached to the 5' end of the inserted coding region of the IL-1 gene.

A preferable shuttle vector for carrying out the present invention is designated as pY ADH. As illustrated schematically in FIG. 5, the copy DNA expression in *E. coli*, and an ampicillin ("Amp$^R$") resistant gene for selection of transformed *E. coli* cells. The shuttle vector also includes the 2u circle origin of replication and a yeast Trp I gene for selection of transformed yeast hosts in yeast (trp minus) auxotrophs. The shuttle vector further includes the yeast promoter sequence from the alcohol dehydrogenase gene ("ADH") for propagation of the plasmid in both yeast and *E. coli* hosts. This promoter sequence is especially advantageous for use in the present invention due to the high level expression of this gene in yeast, and because the complete DNA sequence of this gene is known. All protein coding sequences, including the initiator ATG codon, have been removed from the ADH promoter fragment. The pY ADH shuttle vector includes a number of unique substrate sites for cleavage with restriction enzymes, i.e., Eco RI and Stu I.

As illustrated in FIG. 5, the pY ADH IL-1 plasmid is prepared as an expression vector for expression of IL-1 gene by insertion of the coding region of the IL-1 gene in plasmid pY ADH. Samples of this shuttle vector are on deposit with the American Type Culture Collection ("ATCC"), 12361 Parklawn Drive, Rockville, Md. 20852, under Accession No. 39967. This deposit was made on 21st Dec. 1984 and is of plasmid pY ADH IL-1 in *E. coli* strain RR1. The coding region of the IL-1 gene is removed from the cDNA plasmid, prepared above. Due to the absence of a unique restriction enzyme cleavage site at precisely the 5' end of the coding region of the IL-1 gene, a major portion of the coding region is cleaved from the plasmid cDNA with the restriction enzymes Hpa II and Pst I. The Hpa II site is located slightly downstream from the 5' end of the gene coding region. Thereafter, a synthetic oligonucleotide containing the cleaved 5' end of the gene is chemically synthesized with a HPa II cohesive 3' terminal for convenient ligation to the "natural" major IL-1 cDNA fragment. Since, as noted above, all protein coding sequences downstream from the ADH promoter sequence were removed, the synthetic oligonucleotide is synthesized with an ATC initiation codon at its 5' end.

The IL-1 cDNA fragment together with the synthetic oligonucleotide are inserted in shuttle vector pY ADH which previously has been digested with appropriate restriction enzymes corresponding to the configurations of the 5' terminal of the synthetic oligonucleotide and the 3' terminal of the major IL-1 cDNA fragment. The resultant recombinant shuttle vector pY ADH IL-1 is used to transform a prokaryotic host, e.g, *E. coli*, for high copy amplification of the shuttle vector. After this initial transformation process, the recombinant shuttle vector is isolated from the *E. coli* host and then employed to transform a eukaryotic host, e.g., yeast cells, for high level expression of IL-1. The transformed yeast hosts are harvested and the resulting supernatant is assayed for biological activity utilizing the above described thymocyte proliferation and/or IL-1 conversion assays.

Claimed is:

1. A pharmaceutical preparation consisting essentially of an amount effective in the stimulation of the maturation of prothymocytes of the 25K IgE-bf having the amino acid sequence with the SEQ ID No. 1, or a pharmaceutically acceptable salt of said 25K IgE-bf in essentially pure form or in combination with a pharmaceutically acceptable carrier, and of IL-1 or a pharmaceutically acceptable salt of IL-1 in essentially pure form or in combination with a pharmaceutically acceptable carrier.

2. A pharmaceutical preparation according to claim 1 which comprises the human 25K IgE-bf having the amino acid sequence with the SEQ ID No. 1.

3. A pharmaceutical preparation according to claim 1 which comprises recombinant IL-1.

4. A pharmaceutical preparation according to claim 3 which comprises recombinant IL-1$\beta$.

5. A pharmaceutical preparation according to claim 1 which comprises human IL-1.

6. A pharmaceutical preparation according to claim 5 which comprises recombinant human IL-1$\beta$.

7. A pharmaceutical preparation comprising a ratio of about 50 units of IL-1, or a pharmaceutically acceptable salt thereof, in essentially pure form or in combination with a pharmaceutically acceptable carrier, to about 0.25 up to 125 ng of (b) 25K IgE-bf having the amino acid sequence with the SEQ ID No. 1, or of said pharmaceutically acceptable salt of said IgE-bf$_1$ in essentially pure form or in combination with a pharmaceutically acceptable carrier.

8. A pharmaceutical preparation according to claim 7 wherein said ratio is about 50 units of (a) IL-1 or a pharmaceutically acceptable salt thereof, to 25 up to 100 ng of (b) 25K IgE-bf having the amino acid sequence with the SEQ ID No. 1, or of said pharmaceutically acceptable salt of said IgE-bf.

9. A pharmaceutical preparation according to claim 1 in dosage unit form.

10. A pharmaceutical preparation according to claim 1 for parenteral application.

11. A pharmaceutical preparation according to claim 1 for intravenous application.

12. A process for the manufacture of a pharmaceutical preparation according to claim 1 which process comprises mixing said IL-1 or a pharmaceutically acceptable salt thereof and said 25K IgE-bf having the amino acid sequence with the SEQ ID No. 1, or said pharmaceutically acceptable salt of said IgE-bf with a pharmaceutically acceptable carrier.

13. A pack comprising a pharmaceutical preparation according to claim 1 together with instructions for its use.

14. A kit comprising in discreet containers
  (a) a composition of essentially pure 25K IgE-bf having the amino acid sequence with the Seq. ID No. 1 or a pharmaceutically acceptable salt thereof, alone or in admixture with a pharmaceutically acceptable carrier therefor; and
  (b) a composition of essentially pure IL-1 or a pharmaceutically acceptable salt thereof, alone or in admixture with a pharmaceutically acceptable carrier therefor,
wherein said component (a) and said component (b) may be used together or sequentially.

* * * * *

UNITED STATES PATENT AND TRADEMARK OFFICE
CERTIFICATE OF CORRECTION

PATENT NO. : 5,236,706
DATED : August 17, 1993
INVENTOR(S) : DEBRE ET AL

It is certified that error appears in the above-identified patent and that said Letters Patent is hereby corrected as shown below:

Column 31, line 39, after "50 units of" insert --(a)-- and line 44, after "of said" replace "$IgE-bf_1$" with --IgE-bf,--.

Signed and Sealed this

Seventh Day of February, 1995

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 174 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
    ( G ) CELL TYPE: Human B. Cells
    ( H ) CELL LINE: CHO cells transformed with pCAL8-BF-ND ( x i ) SEQUENCE DESCRIPTION: SEQ ID NO:1:

```
Leu Arg Met Glu Leu Gln Val Ser Ser Gly Phe Val Cys Asn Thr Cys
 1               5                  10                  15

Pro Glu Lys Trp Ile Asn Phe Gln Arg Lys Cys Tyr Tyr Phe Gly Lys
            20                  25                  30

Gly Thr Lys Gln Trp Val His Ala Arg Tyr Ala Cys Asp Asp Met Glu
        35                  40                  45

Gly Gln Leu Val Ser Ile His Ser Pro Glu Glu Gln Asp Phe Leu Thr
    50                  55                  60

Lys His Ala Ser His Thr Gly Ser Trp Ile Gly Leu Arg Asn Leu Asp
65                  70                  75                  80

Leu Lys Gly Glu Phe Ile Trp Val Asp Gly Ser His Val Asp Tyr Ser
                85                  90                  95

Asn Trp Ala Pro Gly Glu Pro Thr Ser Arg Ser Gln Gly Glu Asp Cys
            100                 105                 110

Val Met Met Arg Gly Ser Gly Arg Trp Asn Asp Ala Phe Cys Asp Arg
        115                 120                 125

Lys Leu Gly Ala Trp Val Cys Asp Arg Leu Ala Thr Cys Thr Pro Pro
    130                 135                 140

Ala Ser Glu Gly Ser Ala Glu Ser Met Gly Pro Asp Ser Arg Pro Asp
145                 150                 155                 160

Pro Asp Gly Arg Leu Pro Thr Pro Ser Ala Pro Leu His Ser
                165                 170
```

( 2 ) INFORMATION FOR SEQ ID NO:2:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

```
Ala Pro Val Arg Ser Leu Asn Cys Thr Leu Arg Asp Ser Gln Gln Lys
 1               5                  10                  15

Ser Leu Val Met
```

20

(2) INFORMATION FOR SEQ ID NO:3:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

```
Ser Leu Val Met Ser Gly Pro Tyr Glu Leu Lys Ala Leu His Leu Gln
 1               5                  10                  15
Gly Gln Asp Met Glu Gln Gln Val Val Phe
                20                  25
```

(2) INFORMATION FOR SEQ ID NO:4:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:4:

```
Ala Pro Val Arg Ser Leu Asn Cys Thr Leu Arg Asp Ser Gln Gln Lys
 1               5                  10                  15
Ser Leu Val Met Ser Gly Pro Tyr Glu Leu Lys Ala Leu His Leu Gln
                20                  25                  30
Gly Gln Asp Met Glu Gln Gln Val Val Phe
                35                  40
```

(2) INFORMATION FOR SEQ ID NO:5:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:5:

```
Ala Pro Val Arg Ser Leu Asn Cys Thr Leu Arg Asp Ser Gly Gln Lys
 1               5                  10                  15
Ser Leu Val Met Ser Gly Pro Tyr Glu Leu Lys Ala Leu His Leu Gln
                20                  25                  30
Gly Gln Asp Met Glu Gln Gln Val
                35                  40
```

(2) INFORMATION FOR SEQ ID NO:6:

(i) SEQUENCE CHARACTERISTICS:
        (A) LENGTH: 62 base pairs (B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:6:

ACTTGTTGTT CCATGTCTTC GCCTTGCAGG TGCAGGGCTT TCAGTTCGTA GGGGCCGGAC     60
AT     62